US010603466B2

(12) United States Patent
Tal

(10) Patent No.: US 10,603,466 B2
(45) Date of Patent: Mar. 31, 2020

(54) INTRAVASCULAR CATHETER WITH POSITIONING MARKERS AND METHOD OF PLACEMENT

(76) Inventor: Michael G. Tal, Great Neck, NY (US)

( * ) Notice: Subject to any disclaimer, the term of this patent is extended or adjusted under 35 U.S.C. 154(b) by 299 days.

(21) Appl. No.: 12/966,082

(22) Filed: Dec. 13, 2010

(65) Prior Publication Data

US 2011/0144620 A1 Jun. 16, 2011

Related U.S. Application Data

(60) Provisional application No. 61/286,127, filed on Dec. 14, 2009, provisional application No. 61/320,044, filed on Apr. 1, 2010.

(51) Int. Cl.
*A61M 25/00* (2006.01)
*A61M 25/01* (2006.01)

(52) U.S. Cl.
CPC .... *A61M 25/0108* (2013.01); *A61M 25/0068* (2013.01); *A61M 25/007* (2013.01); *A61M 25/0029* (2013.01); *A61M 25/0071* (2013.01); *A61M 2025/0008* (2013.01); *A61M 2025/0031* (2013.01); *A61M 2025/0034* (2013.01); *A61M 2025/0037* (2013.01)

(58) Field of Classification Search
CPC ........ A61M 2025/0031; A61M 25/007; A61M 2025/0037; A61M 25/0068; A61M 25/0026; A61M 25/0071; A61M 25/0108
USPC ........ 604/27, 28, 29, 43, 508, 264, 523, 529
See application file for complete search history.

(56) References Cited

U.S. PATENT DOCUMENTS

| | | | | |
|---|---|---|---|---|
| 4,968,306 A | * | 11/1990 | Huss et al. | 604/264 |
| 4,989,608 A | | 2/1991 | Ratner | |
| 5,041,084 A | * | 8/1991 | DeVries et al. | 604/43 |
| 5,221,256 A | * | 6/1993 | Mahurkar | 604/43 |
| 5,380,307 A | | 1/1995 | Chee et al. | |
| 5,817,072 A | | 10/1998 | Lampropoulos et al. | |
| 5,931,829 A | * | 8/1999 | Burbank et al. | 604/502 |
| 5,947,953 A | * | 9/1999 | Ash et al. | 604/508 |
| 6,036,682 A | * | 3/2000 | Lange et al. | 604/529 |

(Continued)

FOREIGN PATENT DOCUMENTS

| | | |
|---|---|---|
| JP | 7-503883 | 4/1995 |
| JP | 2004-501675 | 1/2004 |

(Continued)

OTHER PUBLICATIONS

Bommer et al., Determination of right atrial and right ventricular size by two-dimensional echocardiography, 1979, American Heart Association, Circulation, 60:91-100.*

(Continued)

*Primary Examiner* — William R Carpenter
(74) *Attorney, Agent, or Firm* — Veros Legal Solutions LLP

(57) ABSTRACT

An intravascular catheter may include a distal end for insertion and a proximal end. The distal end for insertion may terminate with a tip. It may define at least two openings, of which one is proximal-most in the distal end. The distal tip may include a first radiopaque marker that is discretely positioned at the proximal-most opening and radiographically distinguishes the proximal-most opening from the rest of the distal end. The distal tip may also include a second radiopaque marker that marks the tip.

12 Claims, 16 Drawing Sheets

(56) References Cited

U.S. PATENT DOCUMENTS

| | | | |
|---|---|---|---|
| 6,117,125 | A | 9/2000 | Rothbarth et al. |
| 6,295,990 | B1 | 10/2001 | Lewis et al. |
| 6,482,169 | B1* | 11/2002 | Kuhle ............................ 604/6.16 |
| 6,524,300 | B2 | 2/2003 | Meglin |
| 6,592,565 | B2 | 7/2003 | Twardowski |
| 6,635,027 | B1 | 10/2003 | Cragg et al. |
| 6,682,498 | B2 | 1/2004 | Ross |
| 7,074,213 | B2 | 7/2006 | McGuckin et al. |
| 7,163,533 | B2 | 1/2007 | Hobbs et al. |
| 7,182,746 | B2* | 2/2007 | Haarala et al. .................. 604/43 |
| 7,182,755 | B2 | 2/2007 | Tal |
| 7,316,911 | B2 | 1/2008 | Toombs |
| 7,335,187 | B2 | 2/2008 | Altman |
| D581,529 | S * | 11/2008 | Moehle et al. .............. D24/130 |
| 8,079,973 | B2 | 12/2011 | Herrig et al. |
| 8,323,227 | B2 | 12/2012 | Hamatake et al. |
| 2001/0044622 | A1* | 11/2001 | Vardi ...................... A61F 2/954 606/1 |
| 2002/0188167 | A1* | 12/2002 | Viole et al. ...................... 600/16 |
| 2003/0144623 | A1* | 7/2003 | Heath et al. .................. 604/4.01 |
| 2004/0097880 | A1 | 5/2004 | Schur |
| 2004/0220473 | A1* | 11/2004 | Lualdi ............................ 600/435 |
| 2004/0243095 | A1 | 12/2004 | Nimkar et al. |
| 2005/0021023 | A1 | 1/2005 | Guglielmi et al. |
| 2006/0004316 | A1* | 1/2006 | Difiore et al. ................ 604/6.16 |
| 2006/0004325 | A1* | 1/2006 | Hamatake et al. ............. 604/43 |
| 2007/0060883 | A1 | 3/2007 | Doty |
| 2008/0015499 | A1 | 1/2008 | Warnack |
| 2008/0091140 | A1* | 4/2008 | Hamburger ....... A61M 25/0108 604/93.01 |
| 2008/0154206 | A1 | 6/2008 | Guo et al. |
| 2008/0195046 | A1 | 8/2008 | Altman |
| 2008/0214980 | A1* | 9/2008 | Anand .......................... 604/6.16 |
| 2008/0245371 | A1 | 10/2008 | Gruber |
| 2009/0204052 | A1* | 8/2009 | Nimkar et al. .............. 604/6.16 |
| 2009/0326560 | A1* | 12/2009 | Lampropoulos et al. .... 606/148 |

FOREIGN PATENT DOCUMENTS

| | | |
|---|---|---|
| JP | 2007-503883 | 3/2007 |
| JP | 2007-105240 | 4/2007 |
| JP | 2008-504897 | 2/2008 |
| JP | 2008-539049 | 11/2008 |
| WO | WO 01/70299 A2 | 9/2001 |
| WO | WO 2006/105244 | 10/2006 |
| WO | WO 2009/158060 | 12/2009 |

OTHER PUBLICATIONS

Twardowski et al., Side holes at the tip of chronic hemodialysis catheters are harmful, 2001, The Journal of Vascular Access 2001; 2:8-16.*

International Search Report and Written Opinion for PCT/US2010/059998 dated Aug. 31, 2010.

Baskin et al., "Cavoatrial Junction and Central Venous Anatomy: Implications for Central Venous Access Tip Position," *J. Vasc. Interv. Radiol.* 2008; 19: 359-65.

Tal et al., "Comparison of Side Hole Versus Non Side Hole High Flow Hemodialysis Catheters," Hemodialysis International 2006; 10: 63-67.

Burton, Kirsteen, et al., "Chest Radiography and Echocardiography Predictors of Early Hemodialysis Catheter Dysfunction". Open Journal of Radiology, 2012, 2, p. 57-64.

Twardowski, Zbylut J., et al., "Side Holes at the Tip of Chronic Hemodialysis Catheters are Harmful". The Journal of Vascular Access, 2001, 2, p. 8-16.

Kakkos, Stavros K., et al., "Effectiveness of a New Tunneled Catheter in Preventing Catheter Malfunction: A Comparative Study". Journal of Vascular Interventional Radiology, 19(7): 2008, p. 1018-1026.

Knuttinen, Martha-Grace, et al., "A Review of Evolving Dialysis Catheter Technologies". Seminars in Interventional Radiology. Jun. 2009; 26(2): p. 106-114.

Spector, Marcelo, et al., "Clinical Outcome of the Tal Palindrome Chronic Hemodialysis Catheter: Single Institution Experience". Journal of Vascular Interventional Radiology, 2008; 19: p. 1434-1438.

Petersen, Judy, et al., "Silicone Venous Access Devices Positioned with Their Tips High in the Superior Vena Cava Are More Likely to Malfunction", The American Journal of Surgery, 1999; 178:38-41.

Extended Search Report and Written Opinion in European Patent Application No. 10841489.7 dated Oct. 31, 2013.

Office Action in Australian Patent Application No. 2010337128 dated Feb. 10, 2014.

Office Action in Chines Patent Application No. 2010800620112 dated Oct. 14, 2013.

Japanese Office Action dated Oct. 7, 2014 for Japanese Patent Application No. 2012-544666.

Bishop et al. "Guidelines on the insertion and management of central venous access devices in adults." Technical Report. International Journal of Laboratory Hematology. 2007, 29, 261-278.

M. Tal et al., "Dialysis Catheter Tip Placement: The Functional Tip—A different look at a contentious topic," Endovascular Today, 73-75 (Jun. 2013).

Vesley, Thomas M. "Central Venous Catheter Tip Position: A Continuing Controversy." JVIR. May 2003. 14:527-534.

T. Vesely et al., "Optimizing Hemodialysis Catheter Use," Supp. to Endovascular Today, (Jun. 2-11, 2012.

Office Action dated May 1, 2015 in corresponding Australian Patent Application No. 2010337128 (in five pages).

Office Action dated Oct. 7, 2014 for Japanese Patent Application No. 2012-544666.

* cited by examiner

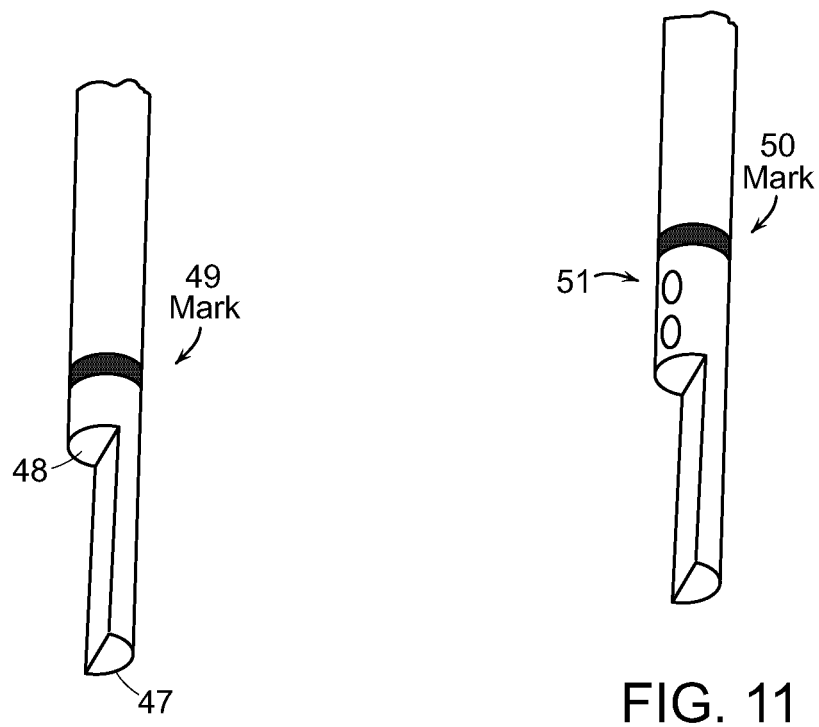
FIG. 10
FIG. 11
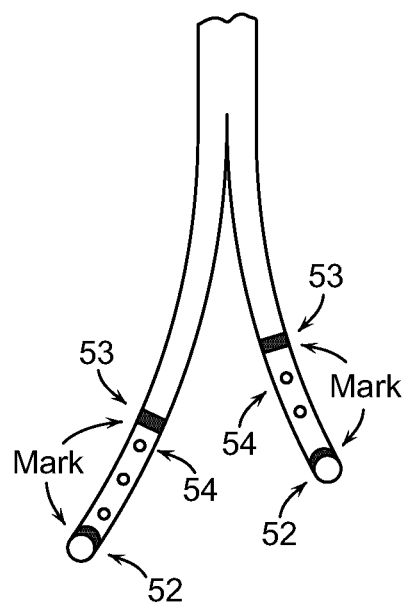
FIG. 12

X-ray 1

X-ray 2

X-ray 3

X-ray 4

INTRAVASCULAR CATHETER WITH POSITIONING MARKERS AND METHOD OF PLACEMENT

CROSS-REFERENCE TO RELATED APPLICATIONS

This application claims the benefit of U.S. provisional application Ser. No. 61/286,127, filed Dec. 14, 2009, and of U.S. provisional application Ser. No. 61/320,044, filed Apr. 1, 2010, the contents of which applications are hereby incorporated herein by reference.

BACKGROUND

There are complications associated with catheter tip position being too low such as perforation of the heart, life threatening arrhythmias and clot formation. Complications related to catheter tip position being too high are also serious and include catheter dysfunction and vascular damage.

The more serious catheter complications such as right atrial thrombus or cardiac perforation and arrhythmias are related to tip position being too low, physically touching the posterior wall or floor of the right atrium. Because of that the FDA issued a statement recommending that the tip of catheter should not be in the heart. On the contrary, tip position too high can compromise catheter function as well as enhance fibrin sheathing and possibly subsequent central venous stenosis. For that reason many physicians prefer inserting the catheter tip into the right atrium. It seems that the catheter tip causes the complications associated with the low catheter placement and the most proximal openings are causing the complications associated with the catheter being placed too high.

Catheter complications are divided into three groups: Infection, thrombosis and fibrin sheathing. These complications are presenting while the catheter is still in the patient. They can present clinically or as catheter dysfunction. Delayed complications are central venous stenosis and occlusion as well as perforation, either of the central veins or the heart. Catheter function is also an important component of dialysis catheters and is influenced by the catheter position.

Side holes are thought to cause damage to the intima or lining of the adjacent vessel. The damage might be caused by the high pressures generated by the dialysis machine trying to aspirate large volumes of blood. This is happening at the proximal side holes of the arterial lumen of the catheter, which are located most proximally. This intimal damage might cause subsequent thrombosis and vascular stenosis.

The functional area of the catheter is between the tip and the most proximal opening. That opening is usually located several centimeters proximal to the tip. Currently, that most proximal opening can not be identified on imaging. The reason for that is that the most proximal opening is not marked and the whole catheter is radio opaque. The operator who wishes to insert the intravascular catheter accurately has no way of knowing where that most proximal opening is and where it is in relationship with the patient body or catheter tip. Also, the insertions of catheters are performed under fluoroscopy which provides at time poor image quality. In addition, some patients are overweight and this also contributes to poor image quality. The operator in these cases has a difficult time identifying the exact location and position of the catheter. The catheter embodiment disclosed in this invention will allow the physician to know exactly were the most proximal opening in the catheter is, where it is in relationship to the catheter tip and where it is to the anatomic markers in the patient's body.

Catheter positioning is usually done by locating the tip of the catheter on x ray or fluoroscopy. The intravascular catheter is usually radio opaque throughout its length. The operator identifies the catheter and catheter tip and positions it accordingly in the patient's body. The patient anatomy is identified on x ray or fluoroscopy. Specifically, the junction between the right atrium and superior vena cava is a common anatomical marker used for catheter placement. Tip position of the dialysis catheter is controversial and problematic. Some state that the tip should be in the superior vena cava, some advocate the right atrium and superior vena cava junction and some state that it should be in the right atrium. An often preferred tip position is one in which the tip of the catheter is at the upper part or middle of the right atrium. The present invention aims to make catheter position easier and more precise. The marker adjacent to the most proximal opening on the catheter will allow the operator to precisely and easily place that marker at the desired place, which can be the superior vena cava and right atrial junction. Since there are many types of catheters on the market and the proximal openings and tip design of these catheters vary considerably, this marker will allow better uniformity and accurate positioning, no matter what kind of catheter is used. Even though the catheter is radio opaque through its length, the radio opaque marker on top of that will allow identification of a particular location on the catheter which will make catheter insertion more precise.

SUMMARY

An intravascular catheter may have a marker on it, which may be radiopaque. The marker may be located at, or adjacent to, the most proximal opening of the catheter and will be seen on imaging. This form of marking allows the user to distinguish the "functional length" of the catheter from the rest of the catheter, to help ensure proper placement.

Methods of placement of an intravascular catheter with a positioning marker or markers are described. The method of placement may enable safe, easy and accurate device placement in the patient's body.

BRIEF DESCRIPTION OF THE DRAWINGS

FIG. 10 depicts the tip of a staggered tip catheter with a double D design without side hole or side openings.

FIG. 11 depicts the tip of a catheter with a double D design with openings in the shorter arterial lumen only.

FIG. 12 depicts the tip of a split tip catheter.

DETAILED DESCRIPTION

An intravascular catheter may include a marker that is visible on imaging. The marker may be placed adjacent to the most proximal opening of the catheter. The marker can be placed at the most proximal opening, proximal to it or distal to it. The marker can be placed on any catheter design. If it is a dual lumen or a split tip design, multiple markers can be placed, one or two on each catheter. The radio opaque marker can be made from any radiopaque material such as tungsten, iodine, lead, barium or any other substance. The radiopaque marker can be placed at different locations on the catheter, preferentially proximal to the most proximal opening (i.e., side hole, side slot, aperture, fenestration, or other liquid-permeable communication). The purpose of the marker may be to allow a physician to accurately determine the position of the catheter in the patient's body. Specifically the operator can align the mark on the catheter with the right atrium\ Superior vena cava junction. This catheter may allow accurate placement and therefore reduce complications caused by intravascular catheters placed too low or too high.

Also disclosed are methods of placement of an intravascular dialysis catheter with markers. The methods are for placement under fluoroscopic guidance. The marker may be seen on x ray imaging. The method is described for acute, non tunneled catheters as well as for chronic, tunneled catheters.

An intravascular catheter may include a distal end for insertion with a first radiopaque marker that is discretely positioned at the proximal-most opening and radiographically distinguishes the proximal-most opening from the rest of the distal end; and a second radiopaque marker that marks the tip.

Figure 19:
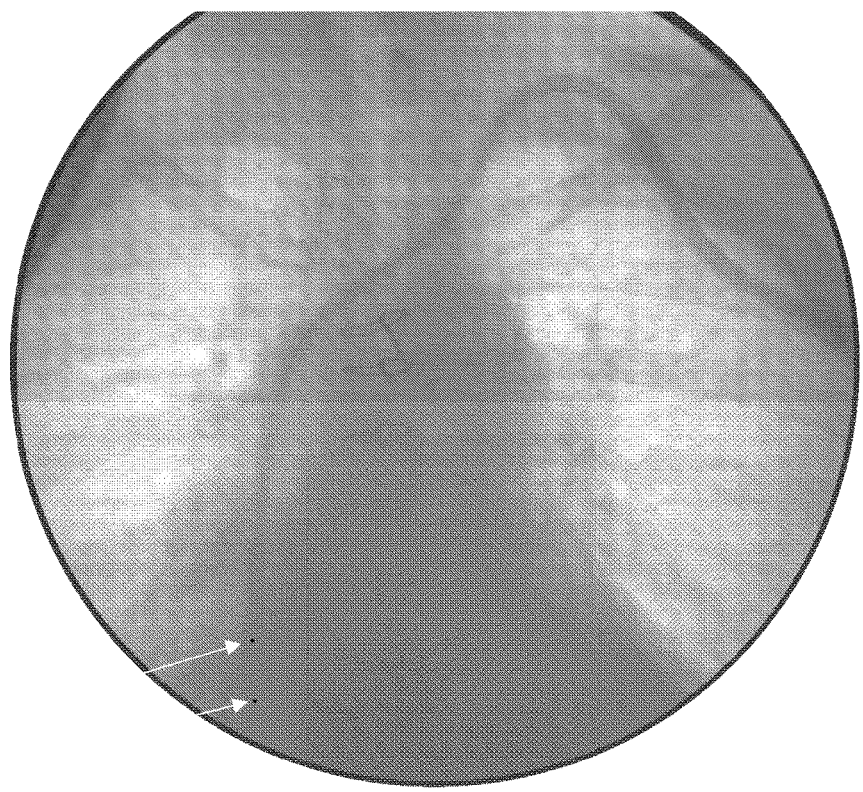
FIG. 19 is an X-ray image showing the catheter placed from the left side with the tip in the right atrium.

An intravascular catheter may be formed such that no opening other than the proximal-most opening is radiographically distinguishable from the rest of the distal end. FIG. 19 is an X-ray image showing the intravascular catheter placed from the left side with the tip in the right atrium. Two positioning markers are seen, one at the proximal side hole and the other at the tip, making the proximal-most opening the only opening radiographically distinguishable.

An intravascular catheter may be formed such that no other radiopaque marker is positioned at a location between the first radiopaque marker and the tip. Alternatively, a catheter can include a third radiopaque marker that makes at least one opening, other than the proximal-most opening, radiographically distinguishable from the rest of the distal end.

An intravascular catheter may be formed such that the distal end has no radiopaque markers other than the first and second radiopaque markers.

An intravascular catheter may be formed such that the second radiopaque marker is discretely positioned at the tip. FIG. 12 depicts the placement of the second radiopaque marker (52) discretely at the tip of a split-tip catheter.

An intravascular catheter may be formed such that the second radiopaque marker marks all or substantially all of the catheter distal end.

An intravascular catheter may be formed such that the distance between the tip and the first radiopaque marker defines a functional catheter length in the range of about 1.5 cm to about 5 cm.

An intravascular catheter may have a functional catheter length of about 3 cm.

An intravascular catheter may be formed such that the first radiopaque marker is positioned in the distal end such that the first radiopaque marker will be located at the junction of a human patient's right atrium and superior vena cava when the catheter is optimally positioned in the patient.

The tip(s) of a catheter may be open or closed. That is, a tip may terminate with an opening, or the tip may terminate without an opening.

Figure 1:
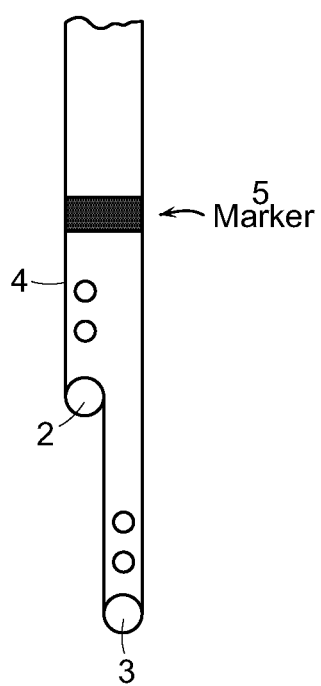
FIG. 1 depicts an intravascular catheter staggered tip design: a double lumen staggered tip catheter.

An intravascular catheter may be formed such that the tip is symmetric, staggered, pointed, tapered to the wire, or split. FIG. 1 depicts a drawing of a dialysis catheter-staggered tip design. This is a double lumen staggered tip catheter. The catheter tip (1) is seen. The arterial lumen which is shorter is usually 2.5 cm shorter then the venous lumen (3). The most proximal side hole (4) is seen. The marker (5) is identified proximal to it.

Figure 2:
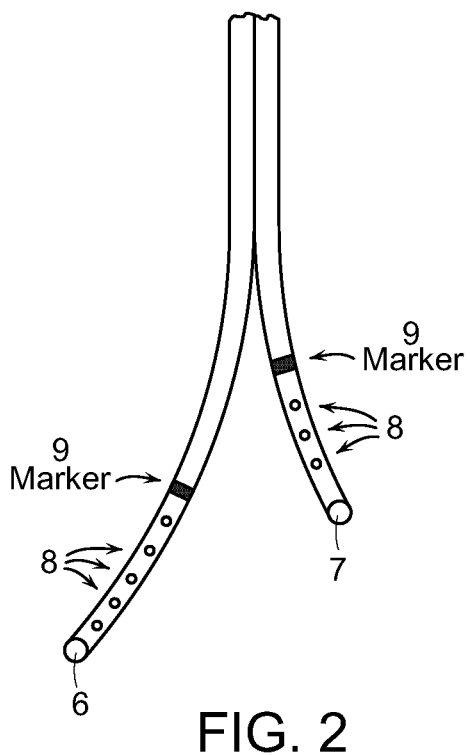
FIG. 2 depicts an intravascular catheter split tip design.
Figure 20:
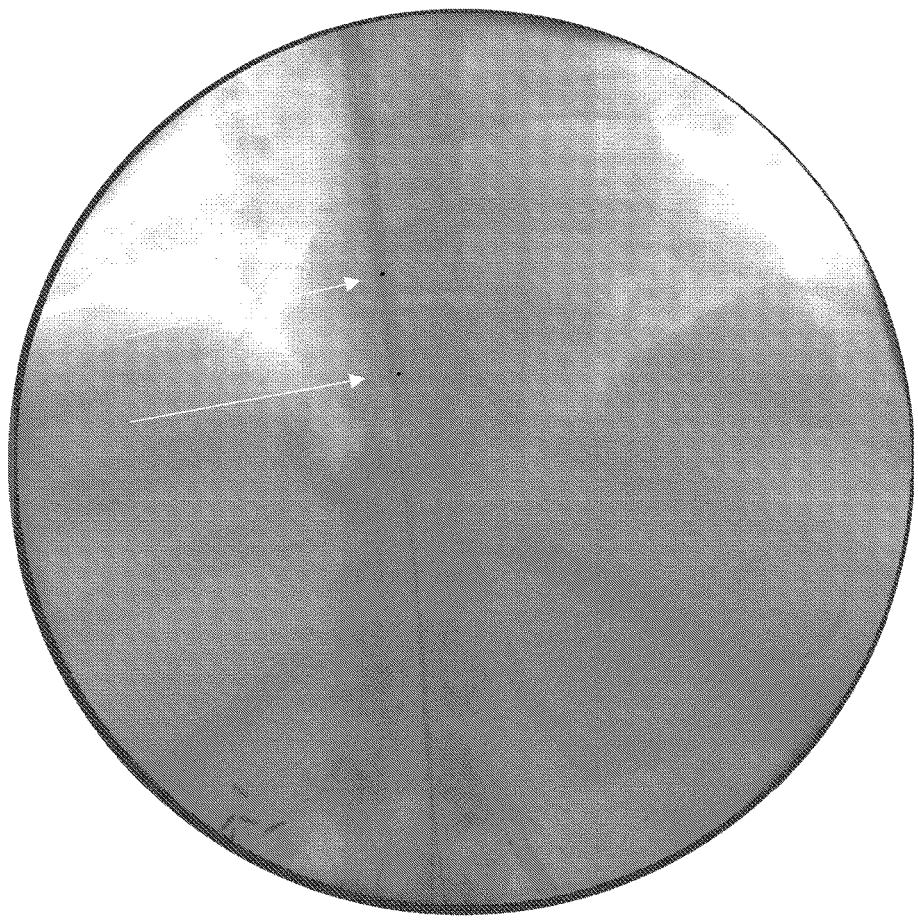
FIG. 20 is an X-ray image showing the catheter placed over a wire.
Figure 22:
FIG. 22 is an X-ray image showing a split tip catheter over a wire with the markers at the proximal side hole and the tip.

FIG. 2 depicts an intravascular catheter tip-split tip design. The tip of the catheter is seen (6). This is the venous lumen which is usually longer. The tip of the shorter arterial lumen is identified (7). Multiple side holes are seen in both lumens (8). Radiopaque markers (9) are placed in each catheter, adjacent to the post proximal opening of the catheter. FIG. 22 is an X-ray image showing a split tip catheter over a wire with the markers at the proximal side hole and the tip. FIG. 20 depicts a catheter placed over a wire. The exact catheter tip position is difficult to see. The markers are shaped like a dot and placed at the proximal hole and tip. The markers make the catheter position easy to identify.

Figure 3:
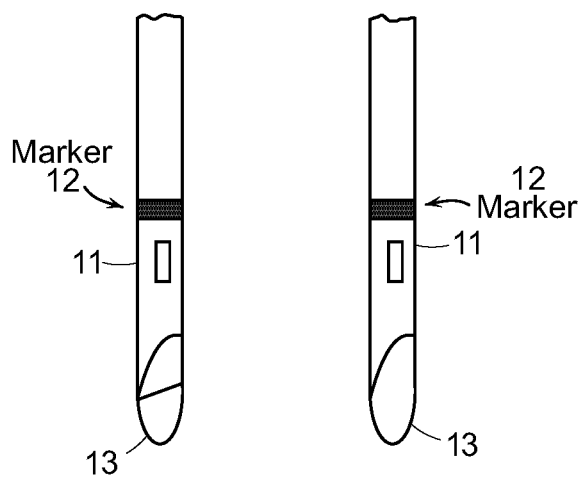
FIG. 3 depicts a symmetrical intravascular catheter with a spiral tip design.
Figure 4:
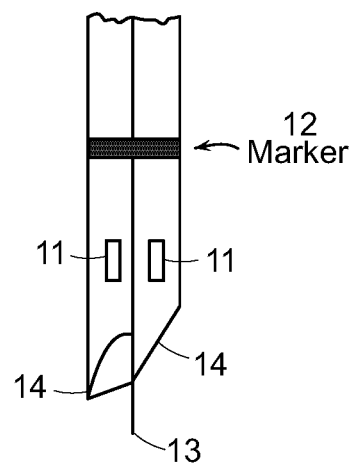
FIG. 4 depicts a symmetrical intravascular catheter with a spiral tip design (lateral view).

FIG. 3 depicts a symmetrical catheter with a spiral tip design. The tip (10) of the catheter is identified. The proximal opening or side slot is seen (11). The marker (12) is identified just proximal to that. FIG. 4 a lateral view of the symmetrical catheter with a spiral tip design. The catheter tip (10) is identified. The distal openings (14) of the catheter are seen. The proximal openings or side slots are seen (11) proximal to the catheter tip. The radiopaque marker (12) is seen proximal to the most proximal openings.

Figure 5:
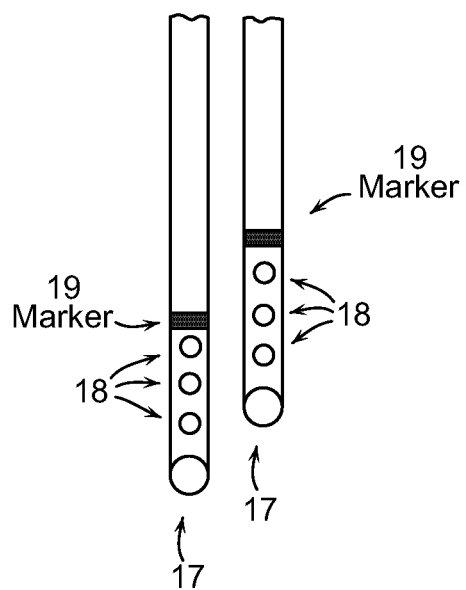
FIG. 5 depicts a double catheter design.

FIG. 5 depicts a double catheter design. Catheter tips are identified (17). Side openings (18) are seen in both catheters. Markers (19) are seen adjacent to the most proximal opening.

Figure 6:
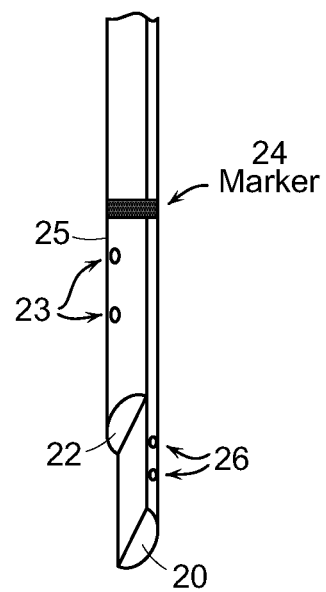
FIG. 6 depicts a double-D staggered catheter design. The venous lumen is longer and extends to the catheter tip.

FIG. 6 depicts a double-D staggered catheter design. The venous lumen is longer and extends to the catheter tip (20).

Openings proximal to the venous lumen are seen (21). The arterial lumen (22) usually is 2-4 cm shorter then the venous lumen. Openings (23) proximal to the arterial lumen are seen. The marker (24) is placed just proximal to the most proximal opening (25).

Figure 7:
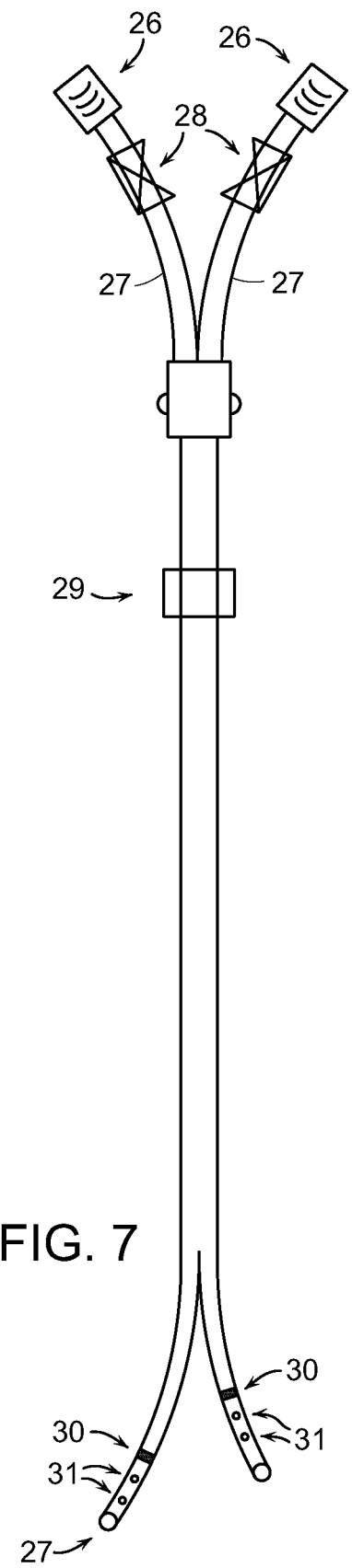
FIG. 7 depicts the whole length of the intravascular catheter. The catheter extends from the proximal hubs to the tip.

FIG. 7 depicts the whole length of an intravascular catheter. The catheter extends from the proximal hubs (26) to the tip (27). The catheter has connection tubing that has a clamp (28) on them. The catheter can have a cuff (29) made from Dacron or other materials for in growth purpose. The radio opaque markers (30) are seen proximal to the side holes (31).

Figure 8:
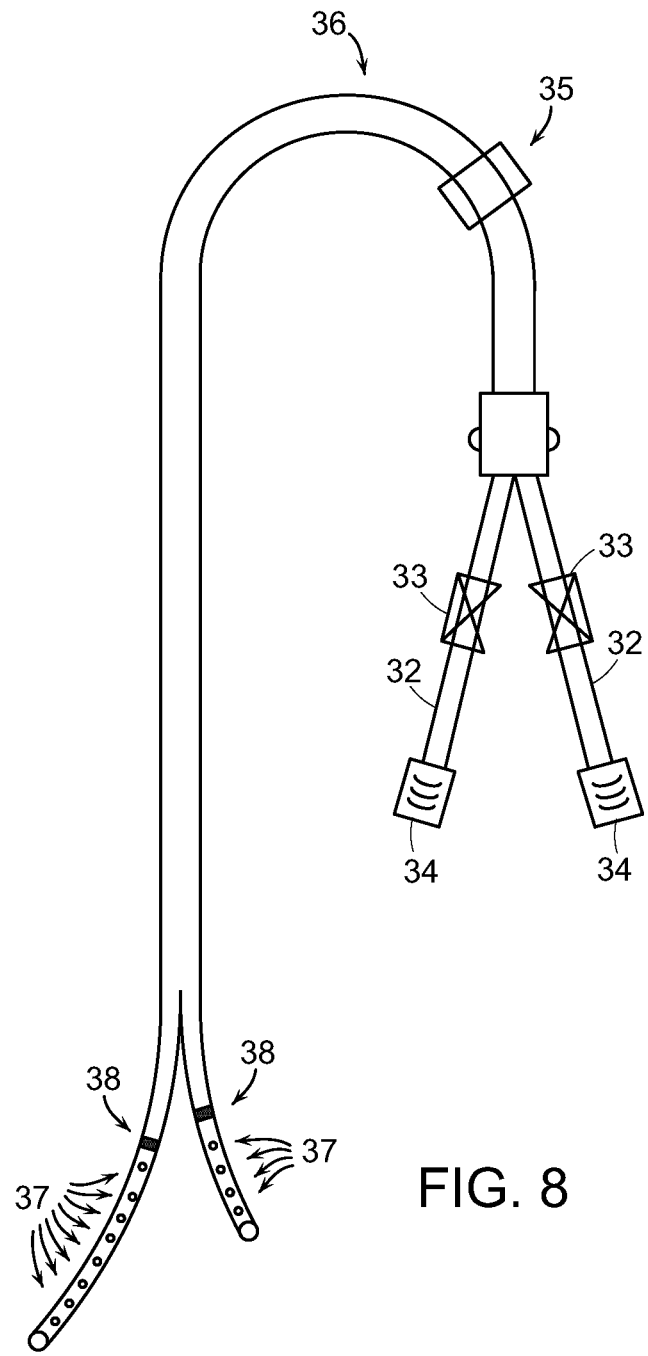
FIG. 8 depicts a split tip catheter that is pre curved.

FIG. 8 depicts a split tip catheter that is pre curved. Connection tubing (32), clamps (33), connection hubs (34), cuff (35) are seen. The curve (36) is seen. Multiple openings exist (37) on the catheter with markers (38) placed proximal to them.

Figure 9:
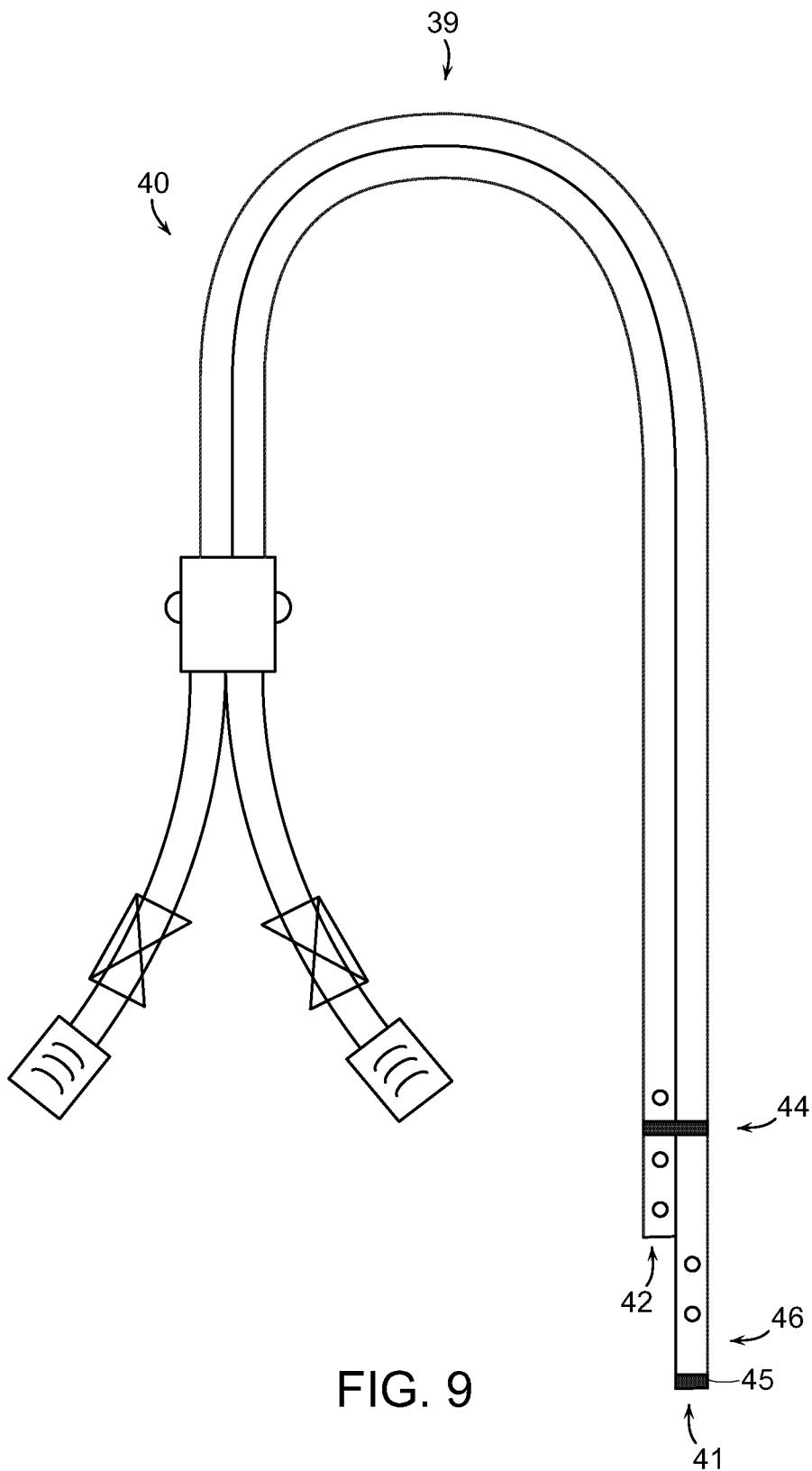
FIG. 9 depicts a staggered tip catheter that is pre curved.

FIG. 9 shows a staggered tip catheter that is pre curved. The curve (39) in the catheter is seen distal to the cuff (40). The venous lumen (41) extends beyond the arterial lumen (42). Side openings in the catheter are seen (43). The first or proximal radio opaque marker (44) is seen adjacent or just distal to the most proximal opening. A second marker (45) is placed at the catheter tip (46).

FIG. 10 shows the tip of a staggered tip catheter with a double D design without side hole or side openings. The venous lumen (47) extends beyond the arterial lumen (48). The radiopaque marker (49) is seen proximal to the opening of the arterial lumen (48).

FIG. 11 shows the tip of a catheter with a double D design with openings in the shorter arterial lumen only. The marker (50) is seen proximal to the most proximal side hole (51).

FIG. 12 depicts the tip of a split tip catheter. Two first radiopaque markers (53) are placed on each lumen. Distal second radiopaque markers (52) are seen at the tips. The proximal markers (53) are seen adjacent to the most proximal side holes (54).

Figure 13:
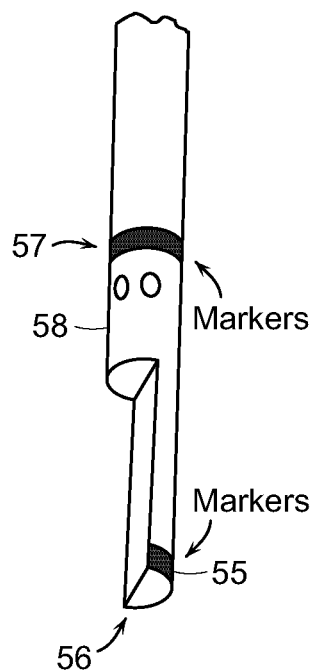
FIG. 13 depicts the tip of a double D staggered tip design with two markers.

FIG. 13 shows the tip of a double D staggered tip design with two markers. The second radiopaque marker (55) is placed at the catheter tip (56). The first radiopaque marker is placed adjacent to the most proximal opening or side hole (58).

Figure 14:
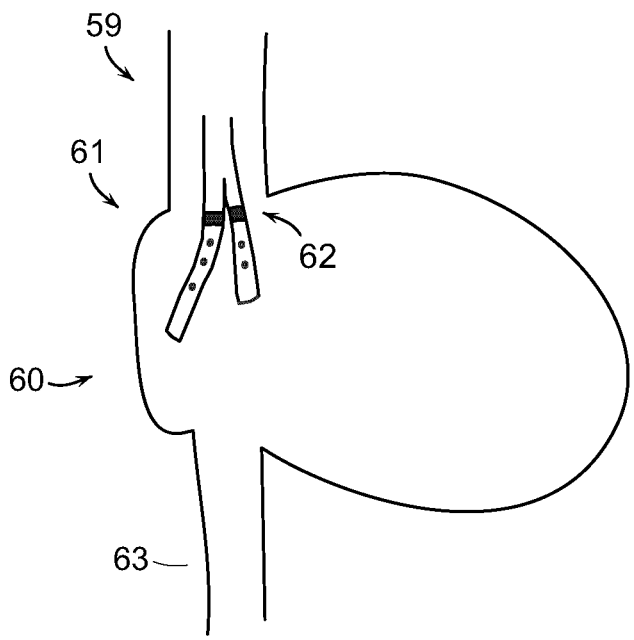
FIG. 14 depicts the preferred positioning of the split tip catheter in the patient's body.
Figure 15:
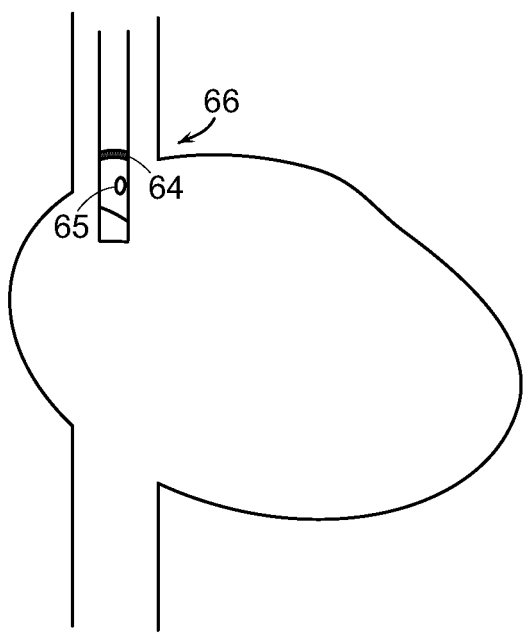
FIG. 15 depicts the preferred position of the symmetric tip catheter in the patient's body.
Figure 16:
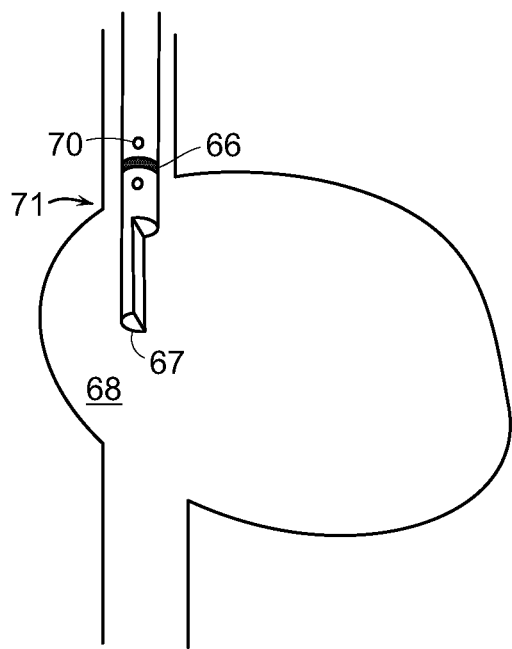
FIG. 16 depicts the position of a staggered tip catheter design in the patient's body.

FIGS. 14 and 15 show split-tip and symmetric catheters, respectively, optimally positioned with the first radiopaque marker (labeled 62, 64 in FIGS. 14 and 15, respectively) located at the junction (61 in FIG. 14) of the right atrium (60 in FIG. 14) and the superior vena cava (59 in FIG. 14), so that, as shown, all openings of the distal end of the intravascular catheter are located in the right atrium. FIG. 16 shows the optimal positioning of a staggered tip catheter design in the patient's body. The catheter tip (67) is located in the right atrium (68). The radio opaque marker (69) is placed adjacent just distal to the most proximal side opening (70). The marker (69) is just above the RA\SVC junction (71).

An intravascular catheter may be formed such that the first radiopaque marker is positioned in the distal end such that the tip will not contact a wall or floor of the right atrium when the catheter is inserted such that the first radiopaque marker is located at the junction of the right atrium and superior vena cava. FIGS. 14, 15, and 16 show the catheter tip not contacting the wall or floor of the right atrium when the first radiopaque marker is located at or adjacent to the junction of the right atrium and the superior vena cava.

An intravascular catheter may be formed such that the first radiopaque marker is sufficiently more radiopaque than the second radiopaque marker as to be radiographically distinguishable from the second radiopaque marker.

Figure 17:
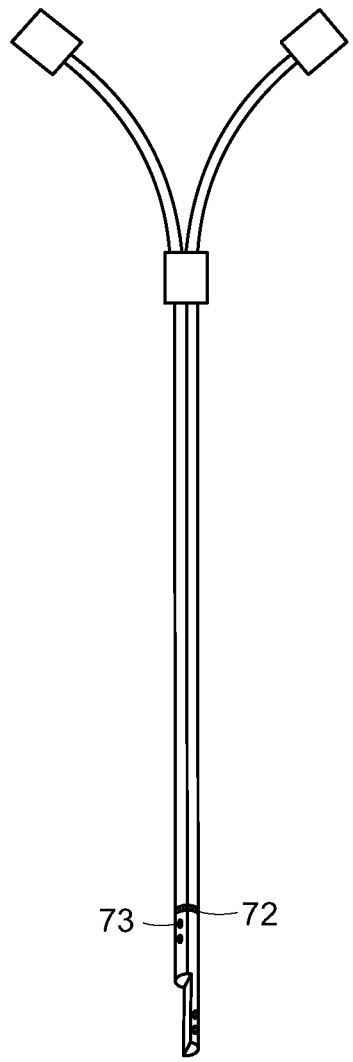
FIG. 17 depicts an acute double lumen catheter with a radio opaque marker.
Figure 18:
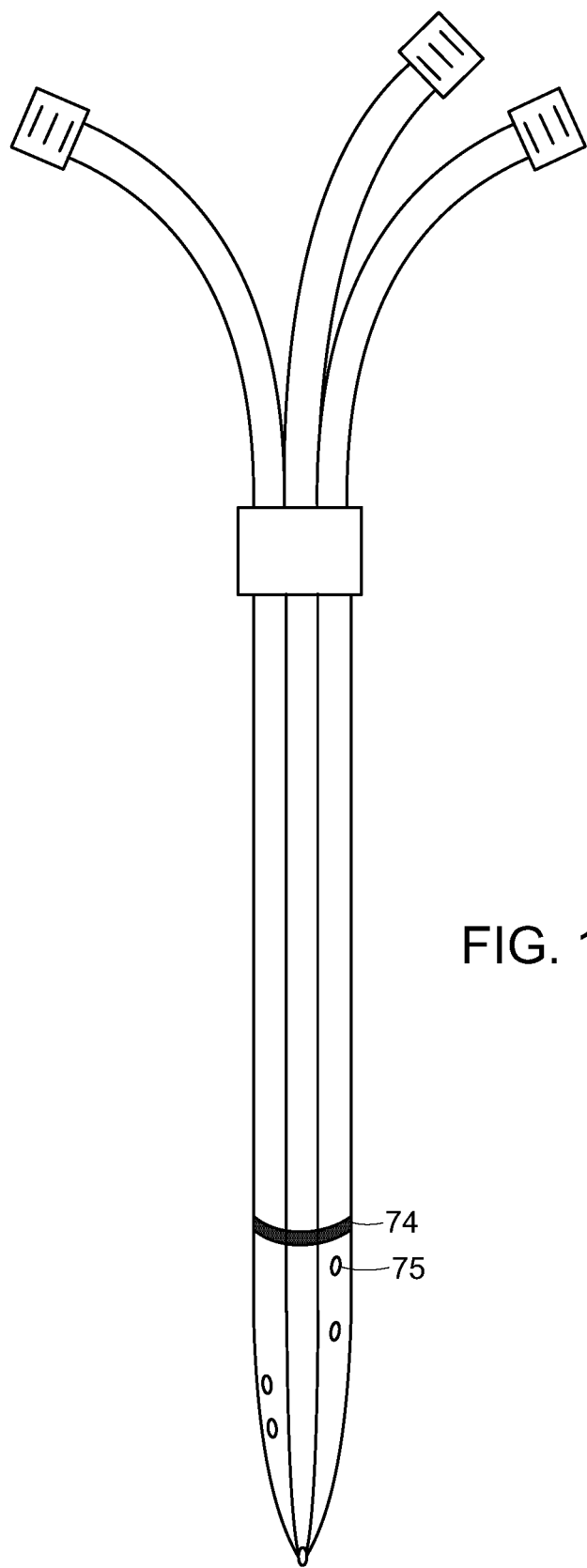
FIG. 18 depicts an acute triple lumen catheter with a radio opaque marker.

An intravascular catheter may be formed such that the distal end for insertion divides into a plurality of lumens. FIG. 17 depicts an acute double lumen catheter. The acute catheter is straight and stiff. The first radiopaque marker (72) is placed adjacent to the most proximal opening in the catheter (73). FIG. 18 depicts an acute triple lumen catheter with a radio opaque marker. The acute catheter has three or more lumens, used for infusion and blood drawings. The marker (74) is placed adjacent to the most proximal side opening (75) on the catheter.

An intravascular catheter may be formed such that the first radiopaque marker is made of tungsten, iodine, lead, or barium.

An intravascular catheter may be formed such that the first radiopaque marker is shaped as a dot, line, or a z-shape.

Figure 21:
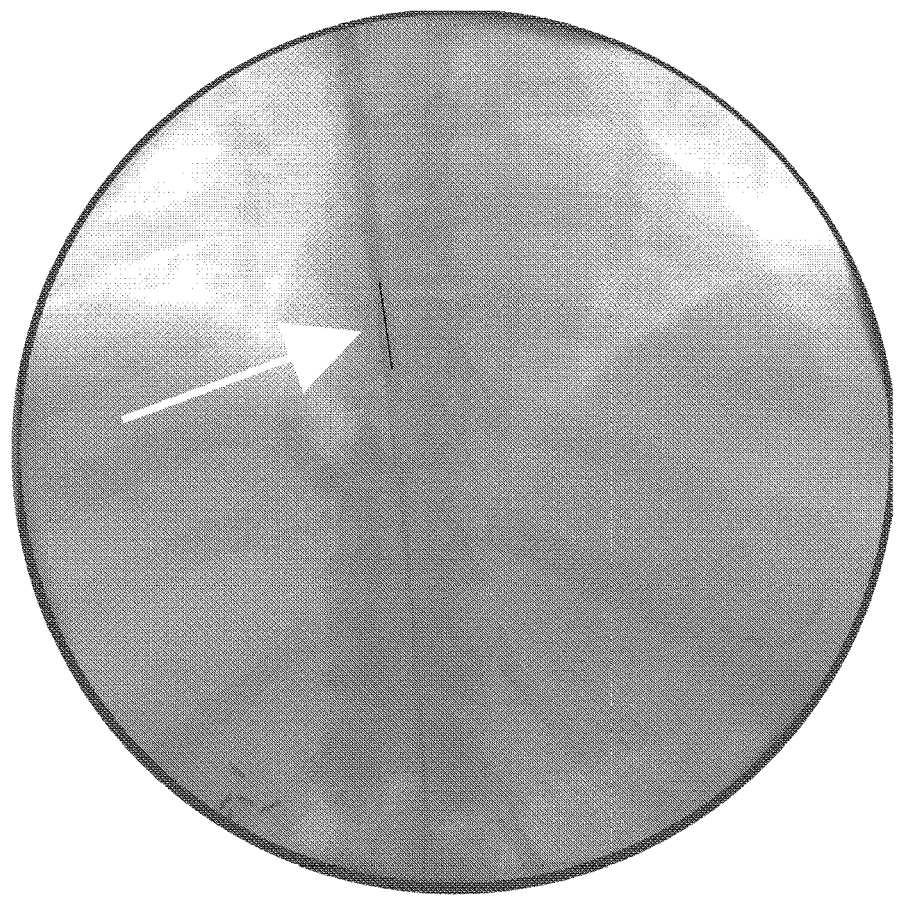
FIG. 21 is an X-ray image showing the catheter over a wire. The marker is shaped as an elongated line, extending from the proximal side hole to the tip.

An intravascular catheter may be formed such that the first and second radiopaque markers together form a radiographically distinguishable line that extends continuously from the proximal-most opening to the tip. FIG. 21 is an X-ray image showing this radiographically distinguishable line extending from the proximal-most opening to the tip. Alternatively, the catheter itself may be radiopaque from the proximal-most opening to the tip.

A medical agent may be infused into a target lumen of a body by inserting an intravascular catheter into the target lumen, injecting the medical agent into a lumen of the intravascular catheter, ejecting the medical agent from the lumen of the intravascular catheter into the target lumen of the body, and assessing the position of the intravascular catheter by radiographically imaging the position of the first radiopaque marker.

An intravascular catheter may be used to treat the human body by advancing the intravascular catheter into the vascular system and assessing the position of the intravascular catheter by radiographically imaging the position of the first radiopaque marker.

An intravascular catheter may be used to treat the human body by advancing any part of the intravascular catheter into the right atrium of the heart and assessing the position of the intravascular catheter by radiographically imaging the position of the first radiopaque marker.

An intravascular catheter may be used to treat the human body by advancing the tip of the catheter into the right atrium of the heart until the first radiopaque marker of the intravascular catheter sits at the junction of the right atrium and the superior vena cava and assessing the position of the intravascular catheter by radiographically imaging the position of the first radiopaque marker.

An intravascular catheter may be used to perform dialysis on a human by advancing the intravascular catheter into the vascular system and assessing the position of the intravascular catheter by radiographically imaging the position of the first radiopaque marker.

An intravascular catheter may be used to perform dialysis on a human by advancing any part of the intravascular catheter into the right atrium of the heart and assessing the position of the intravascular catheter by radiographically imaging the position of the first radiopaque marker.

An intravascular catheter may be used to perform dialysis on a human by advancing the tip of the intravascular catheter into the right atrium of the heart until the first radiopaque marker of the intravascular catheter sits at the junction of the right atrium and the superior vena cava and assessing the position of the intravascular catheter by radiographically imaging the position of the first radiopaque marker.

Examples of specific embodiments of intravascular catheters incorporating the radiopaque markers disclosed herein:

1. Dialysis catheter with a radio opaque mark at the most proximal opening.
2. Dialysis catheter with a radio opaque market proximal to the most proximal opening.
3. Dialysis catheter with two or more radio opaque markers, one of them at or adjacent to the most proximal opening in the catheter. The other marker can be at the catheter tip. Additional positioning markers can be places along the catheter. Alternatively, the catheter itself may be radiopaque from the proximal-most opening to the tip.
4. A double catheter with a positioning marker on each one of the catheters.
5. Split tip, staggered tip, symmetric tip, and any other catheter.
6. Catheter that can be used for pharesis or infusion therapy.
7. Catheter with a clamp.
8. Catheter with connection tubing.
9. Catheter with a Dacron or other material cuff that may allow in-growth and fixation of the catheter to the patient's body.
10. Acute catheter.
11. Catheter that is curved or pre-curved.
12. Acute catheter for acute pharesis or dialysis.

Examples of specific embodiments of markers include:

1. The radio opaque marker may be located preferably at the proximal opening and up to 1 cm from the most proximal opening or side hole in the catheter.
2. The marker can be in the shape of a line extending from the proximal side opening to the catheter tip.
3. The marker can be in the shape of a dot.
4. The marker may be placed such that it will not weaken the catheter or make it more breakable.
5. If it is a dialysis catheter without as proximal openings, the marker can be at the tip or close to the tip.
6. The marker can be placed on acute dialysis and pharesis catheters.
7. The marker or markers can be placed on other locations on the catheter as to make accurate placement more accurate.
8. The marker or markers can be placed in a location that may help the operator accurately place them in an anatomically identified location such as the right atrium and superior vena cava junction.
9. The openings can be of any shape or form, weather round, oval square or diamond shape. They may be of any size, from small to large. The marker may be placed just proximal or at or adjacent to one of those openings.

EXAMPLE

The following are exemplary procedures for placing acute and chronic catheters.

Example 1

For Acute Catheters

Figure 23:
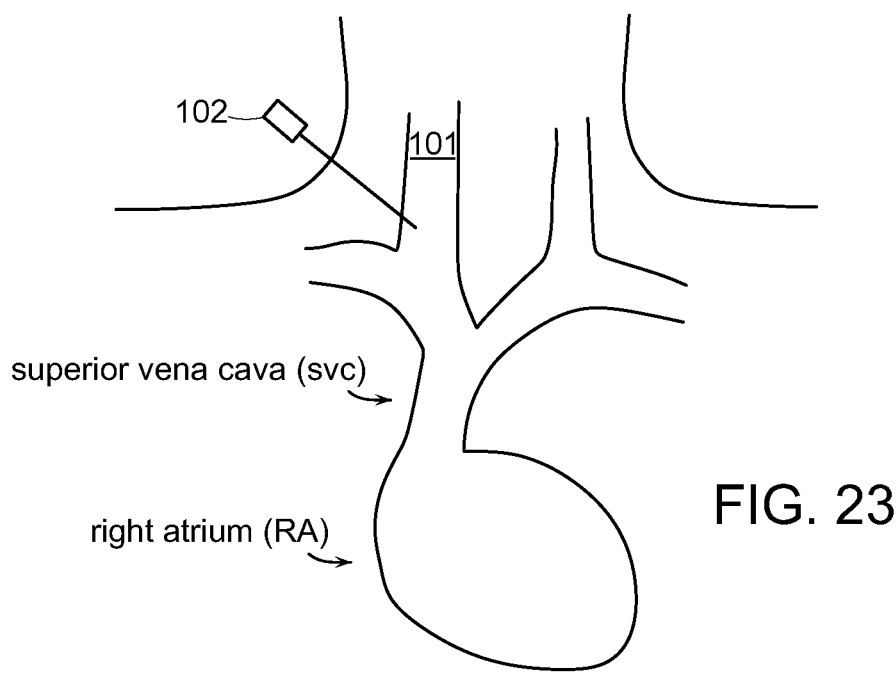
FIGS. 23-34 show steps in various catheter positioning techniques.
Figure 24:
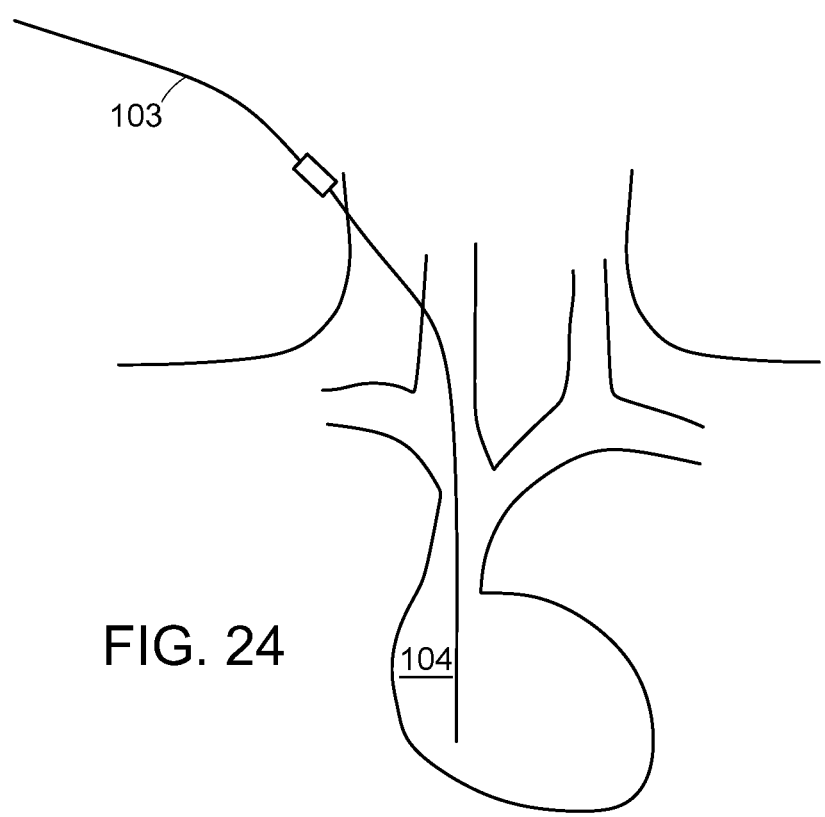
Figure 25:
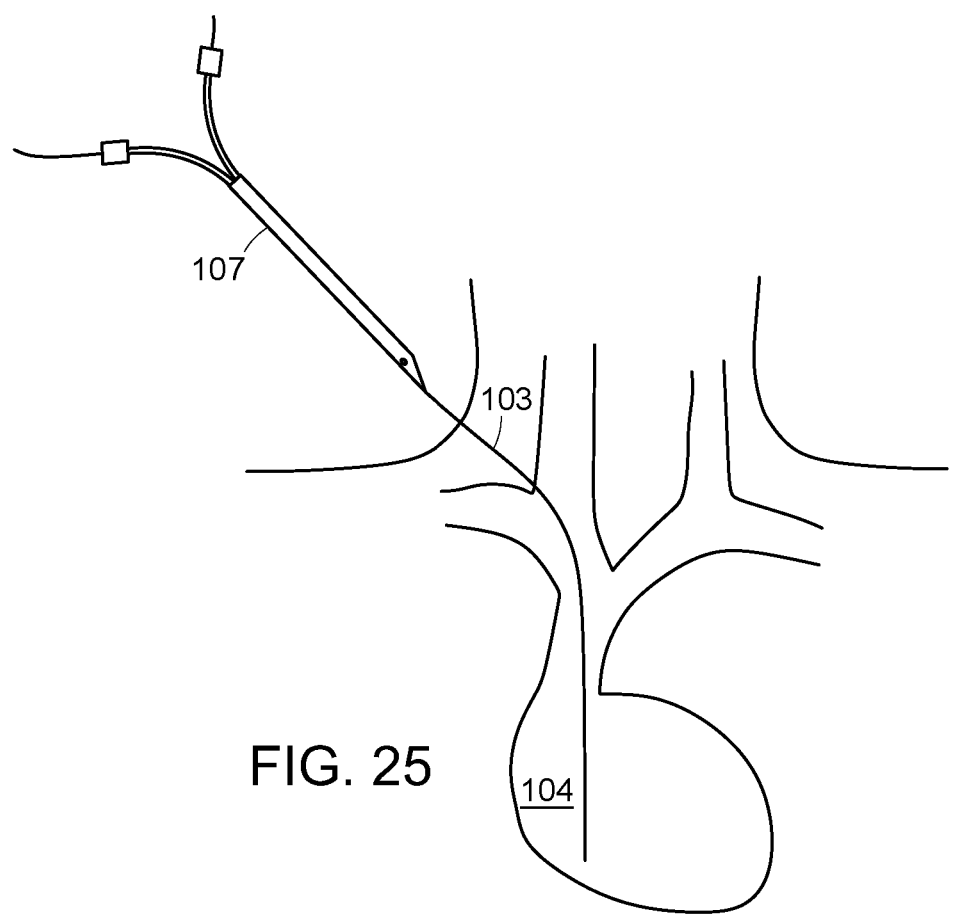
Figure 26:
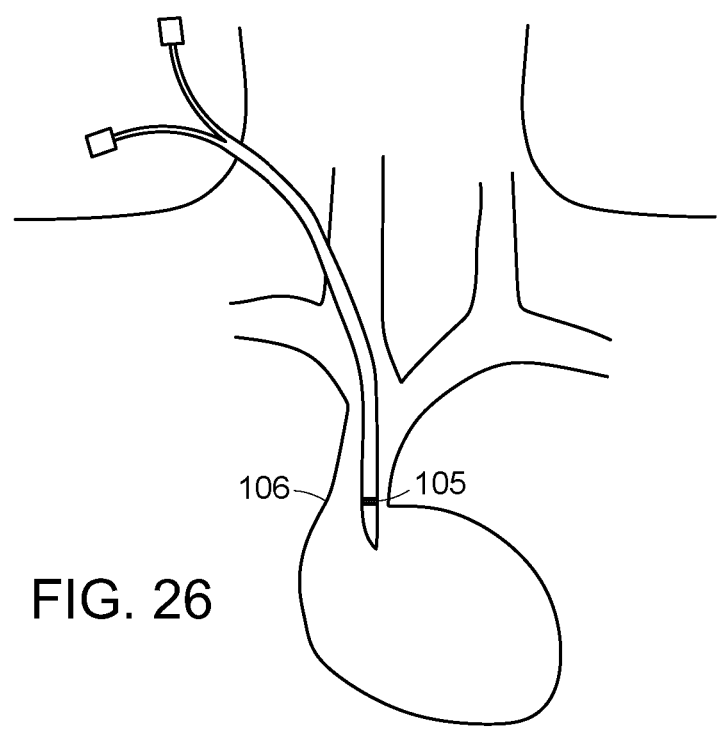

1. Accessing the vein (101) with the needle (102) (FIG. 23). Preferably under ultrasound guidance. The preferred vein is the internal jugular vein, although other veins can be used.
2. Advancing a wire (103) through the needle (FIG. 24). The wire is advanced into the right atrium (104) under fluoroscopic guidance. The wire can be advanced further into the inferior vena cava as well.
3. Removing the needle.
4. Advancing a dilator over the wire to dilate the tissue tract. (optional).
5. Advancing the catheter (107) over the wire (103) into the right atrium (104) under fluoroscopic imaging (FIG. 25).
6. Position the catheter such as that the marker (105) is at the right atrium/Superior vena cava junction (106) (FIG. 26). If there are multiple markers, the top of the most superior marker needs to be positioned at the right atrium/superior vena cava junction.
7. Suturing the catheter to the skin, to prevent it from migration.

Example 2

For Chronic Catheters (First Two Steps Same as Acute)

Figure 27:
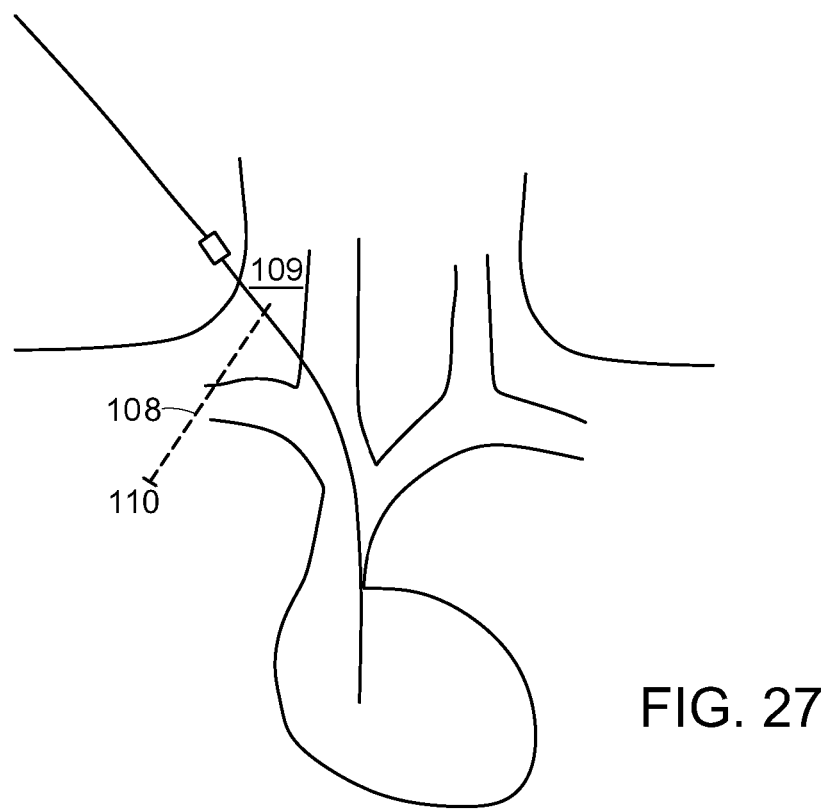
Figure 28:
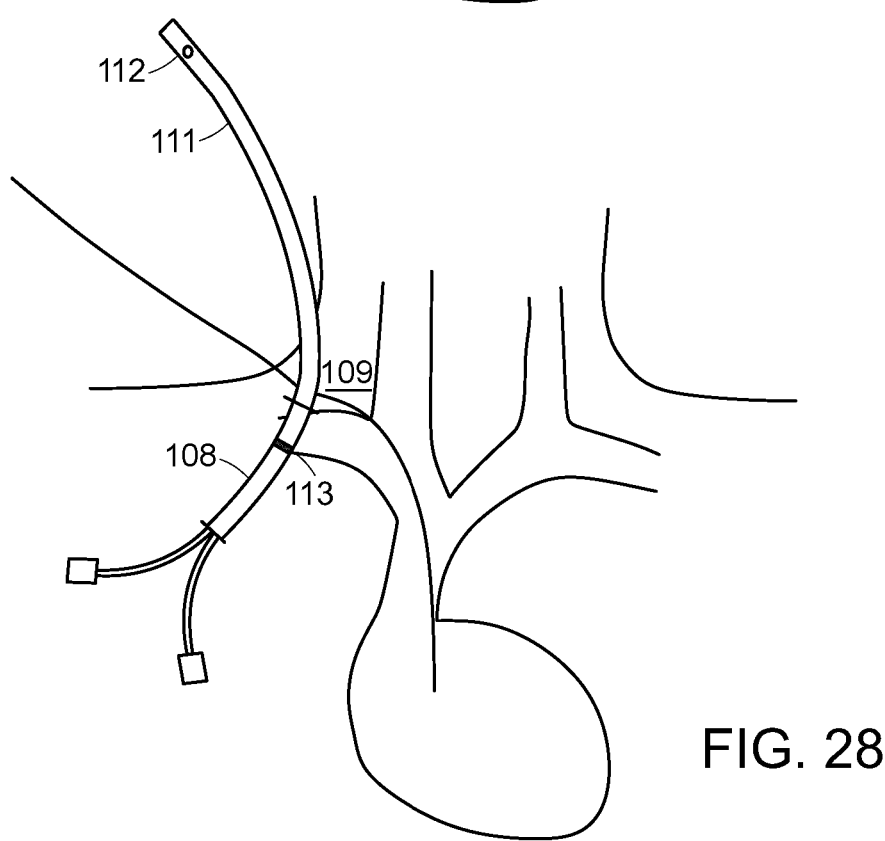
Figure 29:
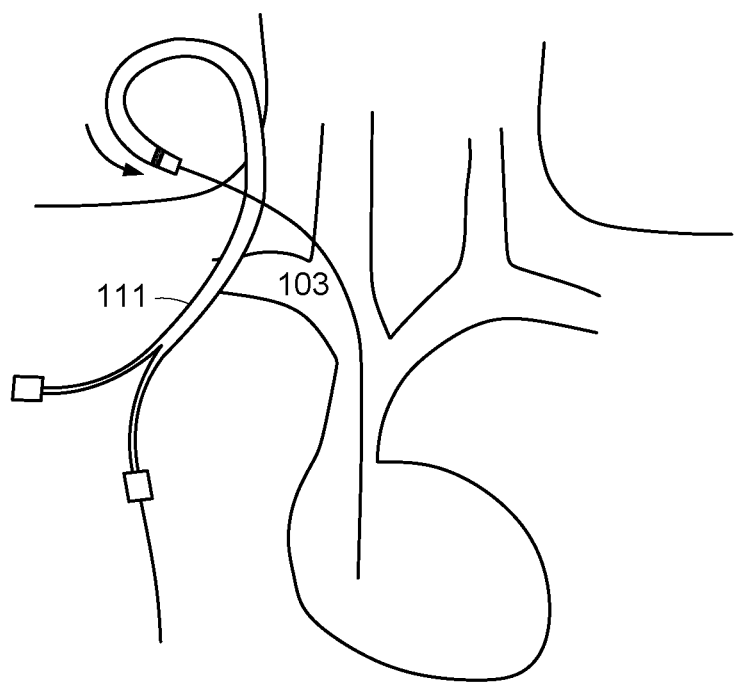
Figure 30:
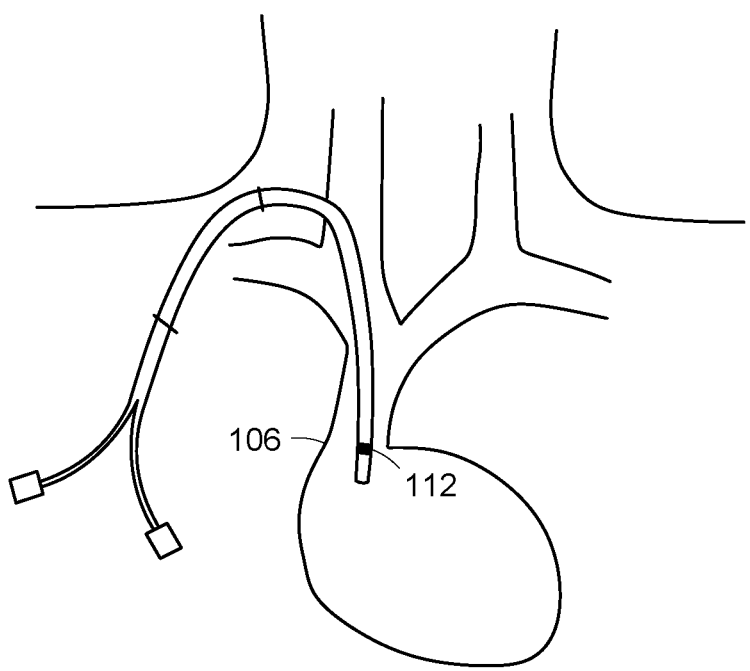

1. Accessing the vein (101) with the needle (102) (FIG. 23). Preferably under ultrasound guidance. The preferred vein is the internal jugular vein, although other veins can be used.
2. Advancing a wire (103) through the needle (FIG. 24). The wire is advanced into the right atrium (104) under fluoroscopic guidance. The wire can be advanced further into the inferior vena cava as well.
3. Creating a subcutaneous tunnel (108) from the vein access site (109) to the catheter skin exit site (110) (FIG. 27).
4. Advancing a catheter (111) with marker (112) under the skin through the tunnel (108) to the vein access site (109) (FIG. 28). This chronic catheter usually has a cuff (113) on it.
5. Removing the needle.
6. Advancing a dilator over the wire to dilate the tissue tract. (optional).
7. Removing the dilator.
8. Advancing a peelable sheath over the wire (optional).
9. Advancing the catheter (111) either through the peel away sheath or over the wire (103) into the right atrium under fluoroscopic imaging (FIG. 29).
10. Positioning the catheter such as that the marker (112) is at the right atrium/Superior vena cava junction (106) (FIG. 30). If there are multiple markers, the top of the most superior marker needs to be positioned at the right atrium/ superior vena cava junction.
11. Suturing the catheter to the skin, to prevent it from migration.

Example 3

Alternative Method of Placement for Chronic Catheters (First Two Steps Same as Acute)

1. Accessing the vein (101) with the needle (102) (FIG. 23). Preferably under ultrasound guidance. The preferred vein is the internal jugular vein, although other veins can be used.
2. Advancing a wire (103) through the needle (FIG. 24). The wire is advanced into the right atrium (104) under fluoroscopic guidance. The wire can be advanced further into the inferior vena cava as well.
3. Removing the needle.
4. Advancing a dilator over the wire to dilate the tissue tract. (optional).
5. Removing the dilator.

6. Advancing a peelable sheath over the wire (optional).

Figure 31:
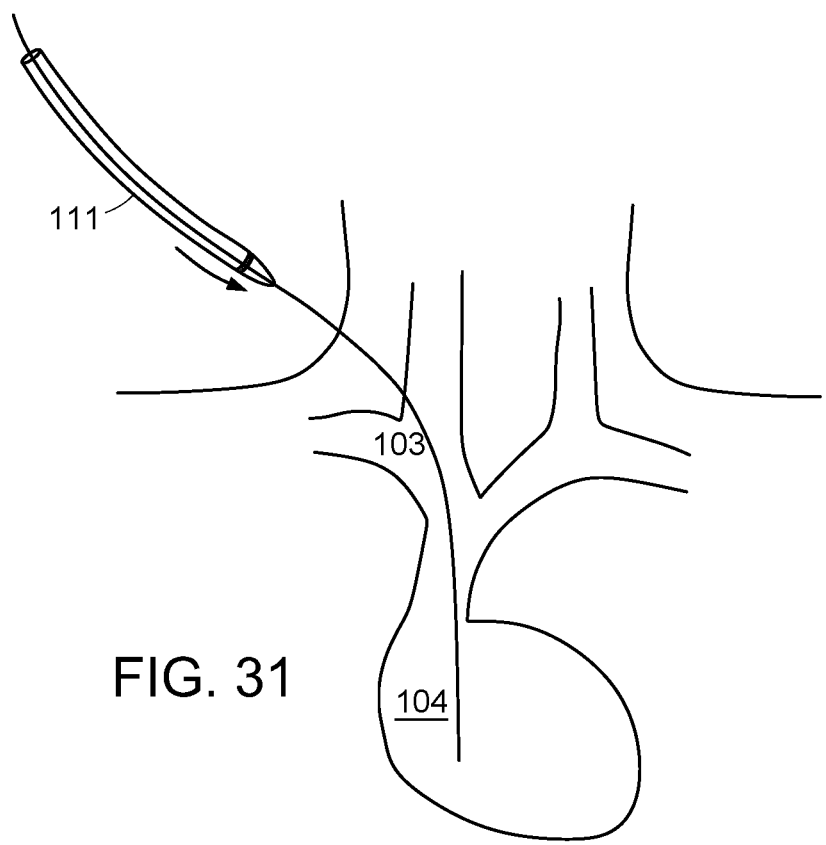

7. Advancing the catheter (111) with marker (112) either through the peel away sheath or over the wire (103) into the right atrium (104) under fluoroscopic imaging (FIG. 31).

Figure 32:
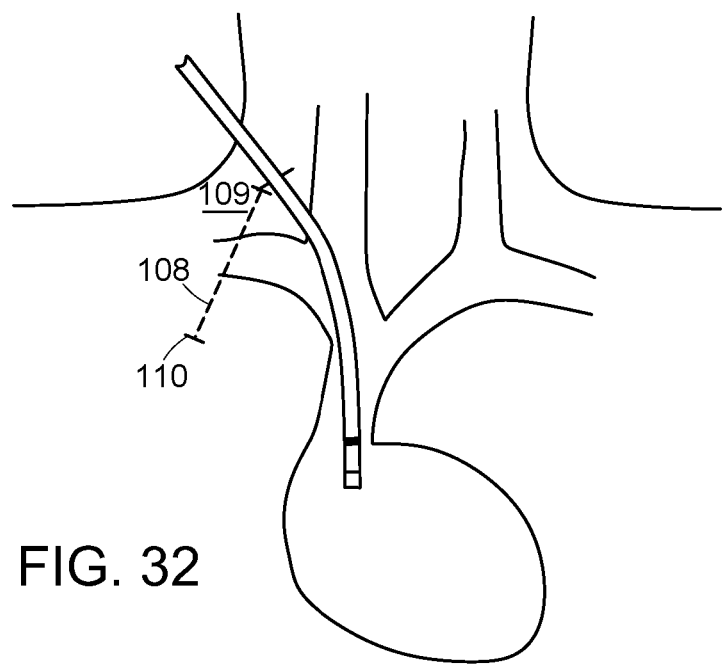

8. Creating a subcutaneous tunnel (108) from the vein access site (109) to a skin exit site (110) (FIG. 32).

Figure 33:
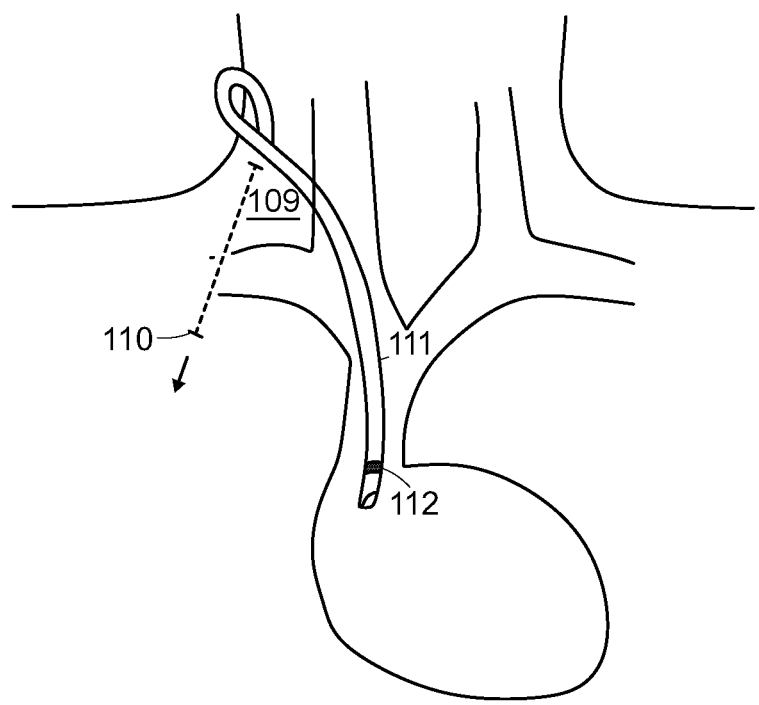

9. Tunneling the catheter (111) with marker (112) from the vein access site (109) to the skin exit site (110) (FIG. 33).

10. Connecting the catheter to a catheter hub.

Figure 34:
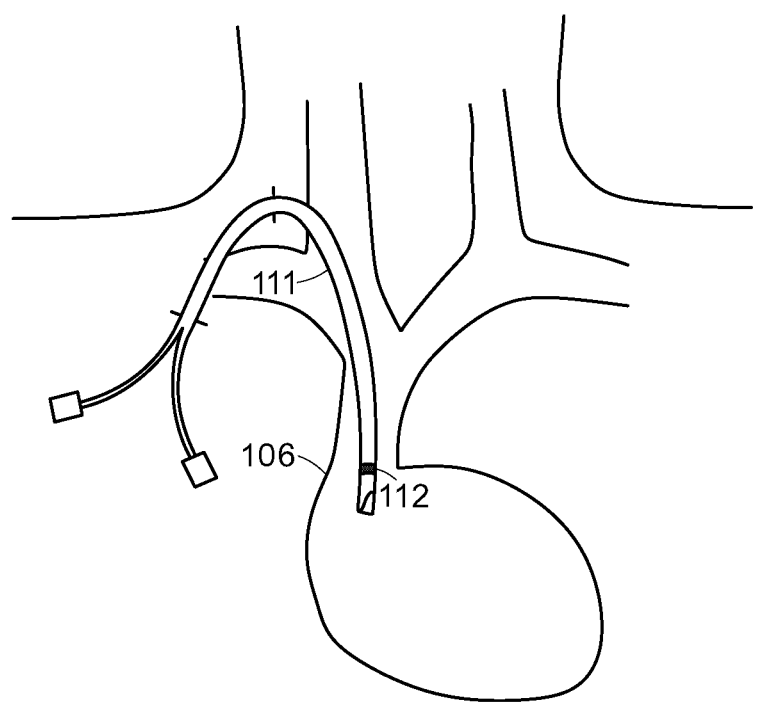

11. Positioning the catheter (111) such as that the marker (112) is at the RA/SVC junction (6) (FIG. 34). If there are multiple markers, the top of the most superior marker needs to be positioned at the right atrium/superior vena cava junction.

12. Suturing the catheter to the skin, to prevent it from migration.

I claim:

1. A method of positioning a dialysis catheter in a human comprising:
   inserting into the human a dialysis catheter comprising:
      a proximal end;
      a distal end for insertion and terminating with a tip;
      at least two lumens extending through the catheter from the proximal end to the tip, at least one lumen of the at least two lumens terminating at a distally facing opening in the distal tip;
      a plurality of side facing openings in the distal end, the plurality of side facing openings in fluid communication with the at least one lumen terminating at the distally facing opening in the distal tip, the plurality of side facing openings located proximal to the distally facing opening, the plurality of side facing openings including a proximal-most side facing opening, the proximal-most side facing opening being the proximal-most side facing opening in the entire distal end; and
      the proximal-most side facing opening associated with a radiopaque marker positioned proximally from and at a distance of 1 cm or less from the proximal-most side facing opening, the radiopaque marker radiographically distinguishing the location of the radiopaque marker from the rest of the distal end, wherein no side facing opening other than the proximal-most side facing opening associated with the radiopaque marker is radiographically distinguishable from the rest of the distal end, wherein the distance between the tip and the radiopaque marker defines a functional length in the range of about 1.5 cm to about 5 cm;
   advancing the distal end of the catheter into the right atrium of the heart until the radiopaque marker is located at or adjacent to the junction of the right atrium and the superior vena cava, so that the entire functional length and all of the openings, including the proximal-most side facing opening, are located within the right atrium; and
   assessing the position of the dialysis catheter by radiographically imaging the position of the radiopaque marker.

2. The method of claim 1, wherein no location other than the approximate location of the proximal-most side opening is radiographically distinguishable from the rest of the distal end.

3. The method of claim 1, wherein no other radiopaque marker is positioned between said radiopaque marker and said distal tip.

4. The method of claim 1, wherein said distal tip comprises no radiopaque marker.

5. The method of claim 1, wherein said radiopaque marker is positioned about 3 cm from said distal tip.

6. The method of claim 1, further comprising performing dialysis on the human using said dialysis catheter.

7. The method of claim 1, wherein advancing said distal tip of said dialysis catheter into the right atrium of the heart comprises:
   accessing a vein with a needle;
   advancing a wire through the needle and into the right atrium;
   creating a subcutaneous tunnel from a vein access site to a catheter skin exit site;
   advancing said distal tip of said dialysis catheter through the subcutaneous tunnel to the vein access site; and
   further advancing said distal tip of the dialysis catheter into the right atrium until said radiopaque marker aligns with said junction of said right atrium and said superior vena cava.

8. The method of claim 1, wherein the distal end of the dialysis catheter further comprises a second radiopaque marker that marks the tip.

9. The method of claim 8, wherein the second radiopaque marker marks all or substantially all of the distal end.

10. The method of claim 8, wherein the radiopaque marker that is discretely positioned proximally from and at a distance of 1 cm or less from the proximal-most side facing opening and the second radiopaque marker together form a radiographically distinguishable line that extends continuously from the proximal-most side facing opening to the tip.

11. The method of claim 1, wherein the at least two lumens comprise two symmetric lumens each including a distally facing opening in the tip and a plurality of side facing openings that are proximal to the distally facing opening.

12. The method of claim 1, wherein the functional length is sized such that the tip will not contact a wall or floor of the right atrium when the radiopaque marker is located at or adjacent to the junction of the right atrium and the superior vena.

* * * * *